United States Patent [19]
Katsuragi et al.

[11] Patent Number: 5,412,442
[45] Date of Patent: May 2, 1995

[54] APPARATUS FOR PHOTOGRAPHING A CORNEAL ENDOTHELIUM

[75] Inventors: Kenjirou Katsuragi; Yoshihiko Hanamura, both of Tokyo, Japan

[73] Assignee: Kabushiki Kaisha Topcon, Tokyo, Japan

[21] Appl. No.: 152,232

[22] Filed: Nov. 16, 1993

[30] Foreign Application Priority Data

Nov. 17, 1992 [JP] Japan .................................. 4-306658

[51] Int. Cl.⁶ .............................................. A61B 3/14
[52] U.S. Cl. ..................................... 351/206; 351/211; 351/214; 351/221; 354/62
[58] Field of Search ............... 606/4; 128/745; 354/62; 364/413.13; 351/205, 206, 208, 211, 214, 216, 220, 221

[56] References Cited
U.S. PATENT DOCUMENTS

| | | | |
|---|---|---|---|
| 4,253,743 | 3/1981 | Matsumura | 354/62 |
| 4,323,299 | 4/1982 | Roberts | 351/214 |
| 4,597,650 | 7/1986 | Yoshino et al. | 351/208 |
| 4,614,411 | 9/1986 | Hörenz | 351/211 |
| 4,976,535 | 12/1990 | Reis | 351/216 |
| 5,262,806 | 11/1993 | Szirth | 351/206 |

Primary Examiner—William L. Sikes
Assistant Examiner—David R. Parsons
Attorney, Agent, or Firm—Finnegan, Henderson, Farabow, Garrett & Dunner

[57] ABSTRACT

An apparatus for photographing an endothelium of a cornea comprising an apparatus optical system including an anterior portion observing optical system for observing the anterior portion of an eye to be tested, an illumination optical system for illuminating the cornea of the eye, and an observing or photographing optical system for observing or photographing the endothelium of the cornea by receiving the light reflected on the endothelium of the cornea which is illuminated by the illumination optical system, the apparatus optical system being provided with a fixation mark light projecting system capable of changing a position where a fixation mark is presented, in order to change a direction in which the eye is fixedly gazed.

13 Claims, 7 Drawing Sheets

← Sectional Direction →
of the Cornea

APPARATUS FOR PHOTOGRAPHING A CORNEAL ENDOTHELIUM

BACKGROUND OF THE INVENTION

1. Field of the Invention

This invention relates to an improvement of an apparatus for observing or photographing an endothelium of a cornea of an eye to be tested by irradiating illumination light toward the cornea.

2. Prior Art

Heretofore, there is known a contact type apparatus as an apparatus for observing or photographing an image of an endothelium of the cornea of the eye. For observing or photographing the endothelium of tile cornea of a person to be tested (patient) using this apparatus, narcotic eye lotion is applied to the eye and then a cone lens is contacted on the surface of the cornea. However, in this contact type apparatus, there is a possibility that the surface of the cornea is damaged by the cone lens. In addition, it has such a shortcoming that much time and labor are required to disinfect the cone lens, and the like.

In view of tile above, a non-contact type apparatus has been developed, in which an optical attachment for observing the endothelium of tile cornea is attached to a slit lamp, and an image of the endothelium is observed or photographed with the aid of this optical attachment.

The non-contact type apparatus is used as follows. The operator (person who examines the eye) roughly adjusts or aligns, by eye measurement, the relative positional relationship between the eye to be tested and tile apparatus optical system. Thereafter, the patient is requested to gaze at a fixation mark and the cornea of the patient is illuminated in that condition. Then, the operator observes or photographs the endothelium of the cornea under the light flux of reflected light from the cornea which is irradiated. In the conventional non-contact type apparatus thus constructed, a fixation lamp serving as the fixation mark is located outside the apparatus body.

This fixation lamp can be moved freely. However, since there is no correlation between the fixation lamp and the apparatus optical system, it is very difficult to make the alignment and the possibility for successfully photographing the endothelium of the cornea is low. This often renders a large burden onto not only the examiner but also the patient.

In the operation for treating, for example, cataract or the like, that an upper part of the cornea is usually cut out in order to insert an intraocular lens therein. Therefore, that part of the cornea which is cut out is damaged. In order to judge recovery of the cornea after an operation, it is necessary to determine how far the cornea has been damaged after the operation compared with the state of the corneas before the operation. However, in the conventional apparatus, this need cannot be satisfied because there is no way to determine which part of the cornea is observed or photographed.

Furthermore, the conventional non-contact type apparatus does not include an optical system adapted to observe the anterior portion with low magnification. As a result, when the endothelium of that part of the cornea other than the central portion of the cornea is observed from the front, it is difficult to determine which part of the cornea is represented by the image of the endothelium under observation because the optical system for observing the endothelium has high magnification.

SUMMARY OF THE INVENTION

It is therefore an object of the invention to provide a non-contact type apparatus for photographing an endothelium of a cornea, in which the endothelium of that part of the cornea other than the central portion of the cornea can be observed or photographed, and that part of the endothelium under observation or photographing can easily be identified.

To achieve the above object, according to the present invention, there is provided an apparatus for photographing an endothelium of a cornea comprising an apparatus optical system including an anterior portion observing optical system for observing the anterior portion of an eye to be tested, an illumination optical system for illuminating the cornea of the eye, and an observing or photographing optical system for observing or photographing the endothelium of the cornea by receiving the light reflected on the endothelium of the cornea which is illuminated by the illumination optical system, the apparatus optical system being provided with a fixation mark light projecting system capable of changing a position where a fixation mark is presented, in order to change a direction in which the eye is fixedly gazed.

According to the present invention thus constructed, since the direction for fixedly gazing at the eye to be tested can be changed, the endothelium of that part of the cornea other than the central part of the cornea can also be observed or photographed. It is also possible to determine an approximate position of the cornea of the eye now under observation or photographing by the anterior portion observing optical system.

Furthermore, since the endothelium of the cornea is photographed under the condition that the patient fixedly gazes at the fixation mark, the eye can be prevented from moving during tile photographing operation to the utmost extent possible, thus making it easier for the operator to photograph the endothelium.

DESCRIPTION OF THE PREFERRED EMBODIMENT

One embodiment of an apparatus for photographing an endothelium of a cornea according to the present invention will be described with reference to FIGS. 1 to 10 inclusive.

Figure 1:
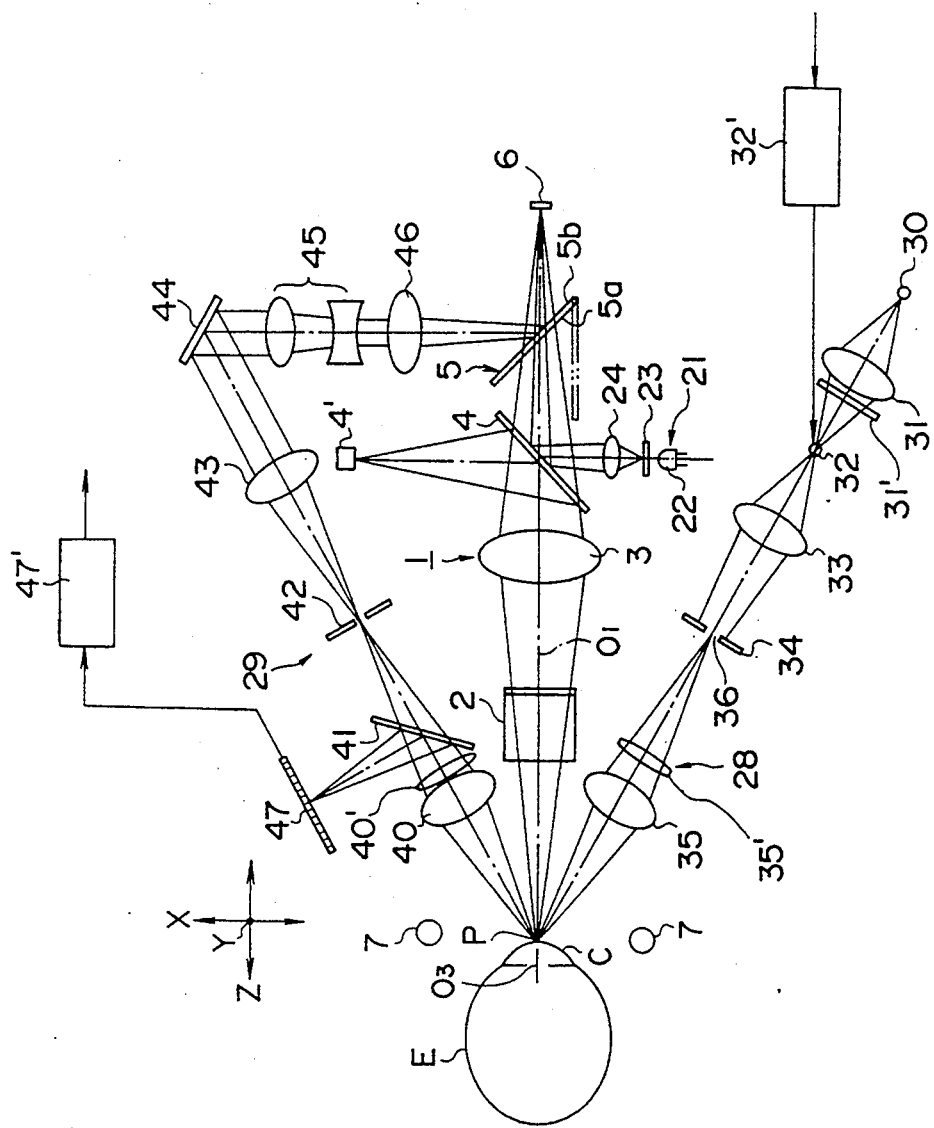
FIG. 1 is a schematic view showing an optical system of an apparatus for photographing an endothelium of a cornea according to the present invention.
Figure 2:
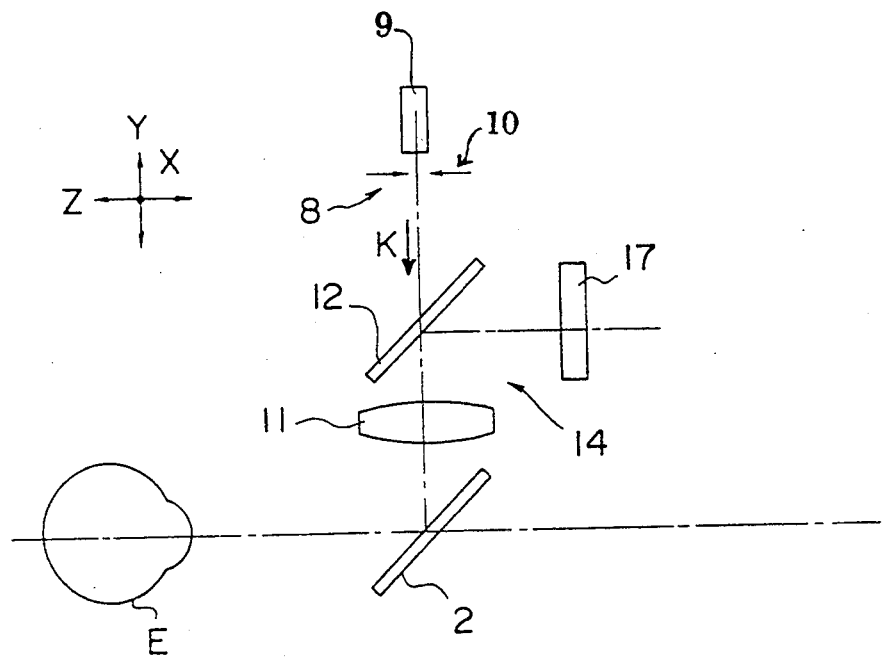
FIG. 2 is a schematic view showing an optical system for projecting an alignment target and an optical system for projecting a fixation mark according to tile present invention.

FIGS. 1 and 2 show an optical system for an apparatus for observing or photographing an endothelium of a cornea. Reference numeral 1 denotes an optical system for observing the anterior portion of an eye E to be tested. This optical system 1 generally comprises a half mirror 2, an objective lens 3, a half mirror 4, an optical path switch mirror 5, and a CCD camera 6. Reference numeral 01 denotes the optical axis of the optical system 1. Reference numeral 7 denotes a light source for illuminating the anterior portion.

The optical path switch mirror 5 has a shading surface 5a and a total reflection surface 5b. The optical path switch mirror 5 is retracted from an optical path of the optical system 1 as shown by the two dots chain line at the time the anterior portion is observed.

The half mirror 2 is commonly used for an optical system 8 (FIG. 2) for projecting a target light for alignment and an optical system 14 for projecting fixation mark light (see FIG. 2). This half mirror 2 reflects the target light for alignment and the fixation mark light toward tile eye E. The optical system 8 includes a light source 9 for the alignment, a pin hole plate 10, a projection lens 11, and a half mirror (or dichroic mirror for transmitting infrared light and reflecting visible light) 12. The light source 9 produces infrared light as target light K. The focal point of the projection lens 11 is coincident with the position of the pin hole plate 10.

Figure 3:
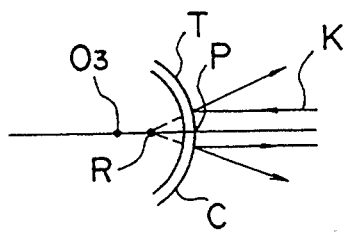
FIG. 3 is a schematic view showing how alignment light flux of the target is reflected.

The target light K emitted from the light source 9 transmits the pin hole plate 10 and the half mirror (or dichroic mirror for transmitting infrared light and reflecting visible light) 12 and made into a parallel light flux by the projection lens 11. After reflected by the half mirror 2, the target light K is guided to the cornea C as shown in FIG. 3. The target light K guided to tile cornea C is reflected by a surface T of the cornea C such that a luminous spot image R is formed at an intermediate location between a vertex P of the cornea C and a center 03 of curvature of the cornea C.

The light flux reflected by the cornea C passes through the half mirror 2 and the objective lens 3 and then guided to the half mirror 4. A part of the light flux reflected by the cornea C is reflected by the half mirror 4 and guided to an alignment sensor 4' as light receiving means (see FIG. 1). A sensor capable of detecting a position such as, for example, PSD (Position Sensitive Device), or the like is used as the alignment detection sensor 4'.

An optical system 21 for projecting a pattern for the use of alignment is disposed at a position opposite to the detection sensor 4' with the half mirror 4 placed therebetween. The optical system 21 comprises a light source 22 for illuminating the pattern for the use of alignment, a circular plate 23, and a projection lens 24. A ring-like pattern for the use of alignment is formed on the circular plate 23. A part of the light flux transmitted the circular plate 23 is reflected by the half mirror 4 and reaches the CCD camera 6. By this, the ring-like pattern for the use of alignment is formed on an image receiving surface of the CCD camera 6.

Figure 4:
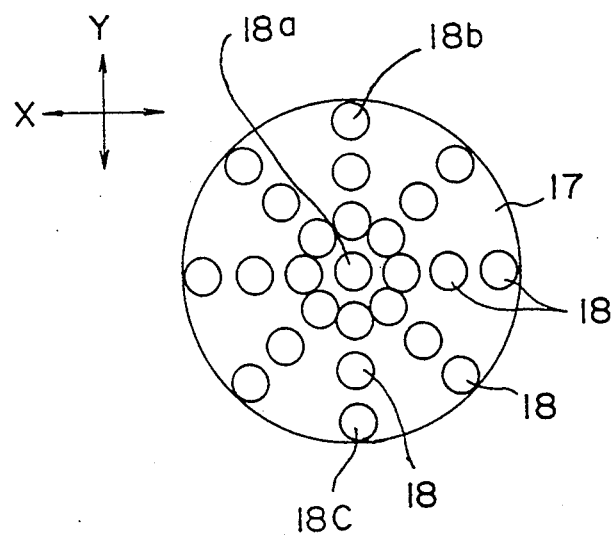
FIG. 4 is a plan view of a first embodiment of a light source for a fixation mark.

The optical system 14 comprises a light source plate 17, a half mirror 12, and a projection lens 11. As shown in FIG. 4, a plurality of light emitting diodes 18 are radially arranged on the light source plate 17 in this embodiment. By selecting one of the plurality of light emitting diodes and emitting the same, the direction of the visual axis of the patient can be changed.

When the light emitting diode 18a is emitted, for example, the patient fixedly gazes at the front surface of the apparatus. When another light emitting diode 18b is emitted, the patient fixedly gazes a direction obliquely right above relative to the optical axis 01.

Figure 5A:
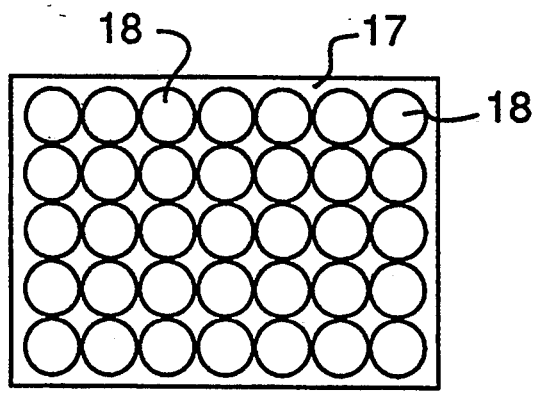
FIGS. 5(a), 5(b), and 5(c) are plan views showing respective alternative embodiments of a light source for a fixation mark.
Figure 5B:
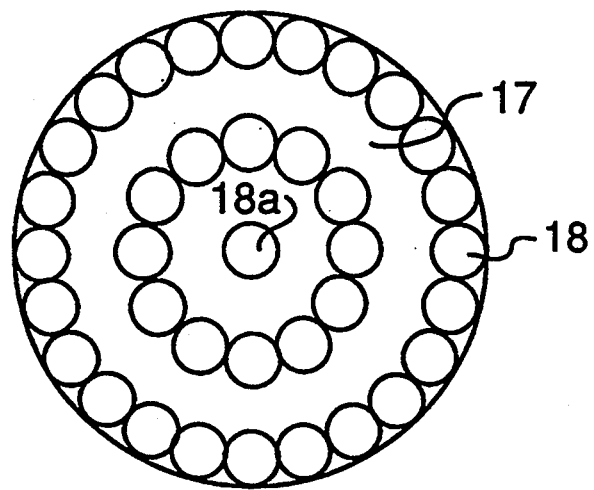
Figure 5C:
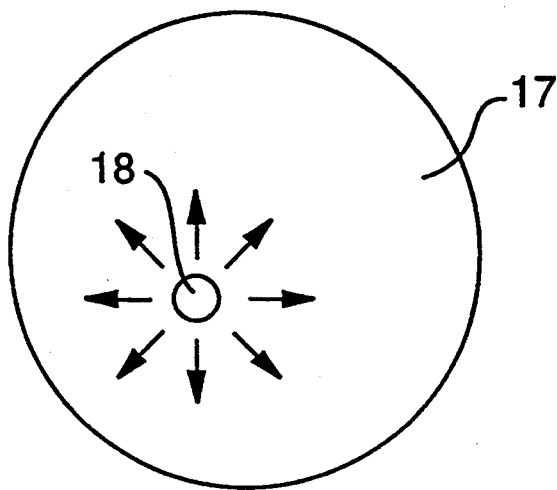

As shown in FIG. 5(a), the light emitting diodes 18 may be two-dimensionally tetragonally arranged on the light source plate 17. Alternatively, as shown in FIG. 5(b), the light emitting diodes 18 may be circularly arranged on the light source plate 17 in concentric relation. Alternatively, as shown in FIG. 5(c), only one light emitting diode 18 may be movably arranged on the light source plate 17.

Figure 6:
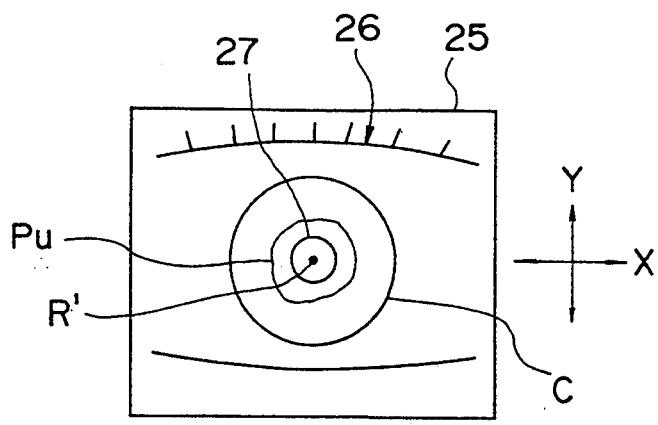
FIG. 6 is a schematic view showing an image of the anterior portion of the eye to be tested at the time the visual axis (sight line) of the patient is directed in an axial direction of the anterior portion observing optical system.

An image of the anterior portion of the eye E illuminated by the light source 7 is formed on the CCD camera 6 through the objective lens 3. The target light for the alignment transmitted the half mirror 4 as well as the pattern light from tile optical system 21 reflected by the half mirror 4 also reaches the CCD camera 6. An image signal from the CCD camera 6 is inputted into a monitor unit. As shown in FIG. 6, an anterior portion image 26 including the cornea C and the pupil Pu of the eye E, a ring-like pattern image 27 and a luminous spot image R' caused by reflection of the target light K are formed on a screen 25 of tile monitor unit.

As shown in FIG. 1, an illuminating optical system 28 and an observing or photographing optical system 29 are disposed on both sides of the optical system 1. The optical system 28 radiates illumination light flux toward the cornea C of the eye E from a slantwise direction. The optical system 28 includes an illuminating light source 30 for the observation, a condenser lens 31, an infrared filter 31', an illuminating light source 32 for photographing, a condenser lens 33, a slit plate 34, a projection lens 35, and a convex lens 35' for correcting the length of the optical path. A halogen lamp is used as the illuminating light source 30, while a xenon lamp is used as the illuminating light source 32. The illuminating light source 30 and the illuminating light source 32 are in conjugate relation relative to the condenser lens 31.

The infrared light flux emitted from the illuminating light source 30 and transmitted the condenser lens 31 and the infrared filter 31' is once converged at the location of the illuminating light source 32. This infrared light flux is guided to the condenser lens 33 as if it were emitted from the illuminating light source 32. Then, the infrared light flux is converged by the condenser lens 33 and guided to the slit plate 34. The light flux emitted from the light source 32 at the time when a photograph is taken, is also likewise guided to the slit plate 34. A rectangular slit 36 elongated in the Y-direction is formed in the slit plate 34. The slit light flux transmitted the slit 36 is guided to the cornea C by the projection lens 35 and transverses the cornea C from its surface T toward the inside.

In this embodiment, the convex lens 35' is inserted into an optical path of the illuminating optical system 28 when the observation is carried out and retracted from the optical path of the illuminating optical system 28 when a photograph is taken. By doing this, the converging position of the light flux on the eye E side becomes constant no matter which one of the light sources 30 and 32 is used. A plane parallel plate or a concave lens may be used instead of the convex lens 35'. In this case, the plane parallel plate or a concave lens is inserted into the optical path of the illuminating optical system 28 at the time a photograph is taken, and tile plane parallel plate or a concave lens is retracted from the illuminating optical system 28 at the time for observation.

The observing or photographing optical system 29 comprises an objective lens 40, a convex lens 40' for the correction of the optical path length, a half mirror 41, a mask 42, a relay lens 43, a mirror 44, a variable lens 45, a focus lens 46, and the optical path switch mirror 5. When the endothelium is observed or photographed, the optical path switch mirror 5 is inserted into the optical path as shown by the solid line of FIG. 1. The function of the convex lens 40' is the same as that of the convex lens 35' of the illuminating optical system 28. The convex lens 40' is also inserted into or retracted from the optical path of the observing or photographing optical system 29 depending on the wavelength.

Figure 7:
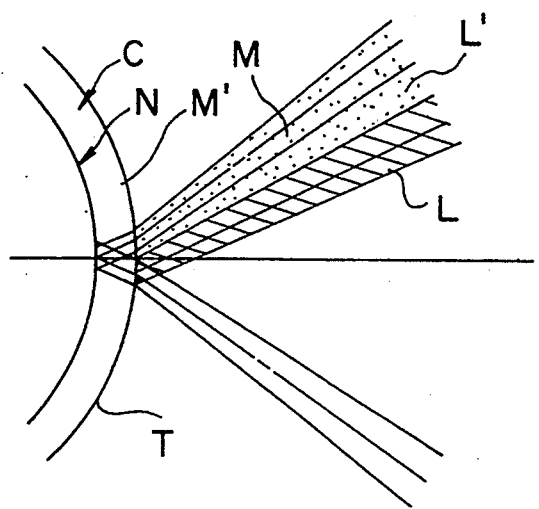
FIG. 7 is a schematic view showing how slit light flux is reflected on the cornea.

FIG. 7 shows how the slit light flux projected by the illuminating optical system 28 is reflected on the cornea C. A part of the slit light flux is first reflected by the corneal surface T as a demarcation surface between air and the cornea C. The quantity of the light flux L reflected from the corneal surface T is largest. The quantity of the light flux M reflected from the corneal endothelium N is comparatively small. Similarly, the quantity of the light flux L' reflected from the corneal substance M' is smallest.

The light flux reflected from the cornea C is converged by the objective lens 40 and guided to the half mirror 41. The reflection light flux transmitted the half mirror 41 is once formed into an image at an area where the mask 42 is located. The mask 42 is adapted to block any surplus reflection light flux excepting the reflection light flux just enough to form the image of the endothelium. The reflection light flux M transmitted by the mask 42 is reflected by the optical path switch mirror 5 through the relay lens 43, the mirror 44, the variable lens 45, and the focus lens 46 to form the image of the endothelium on the CCD camera 6 with high power.

Figure 8:
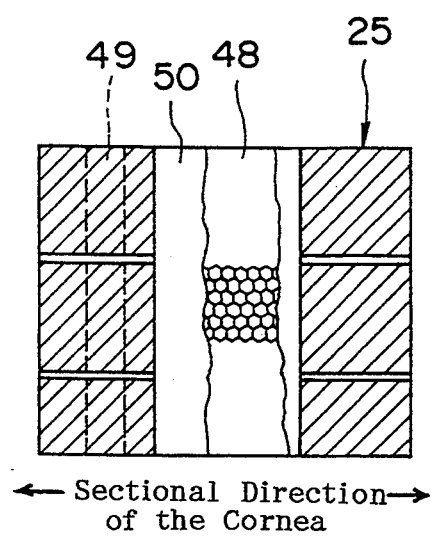
FIG. 8 is a schematic view showing an image receiving state of the endothelium.

As shown in FIG. 8, an image 48 of the endothelium is displayed on the screen 25 of the monitor unit. In FIG. 8, if the area 49 defined by broken lines is not shaded with the mask 42, it represents a luminous image formed by the reflection light flux coming from the corneal surface T. Similarly, the area 50 represents a luminous image formed by the reflection light flux coming from the corneal substance M'.

Figure 9A:
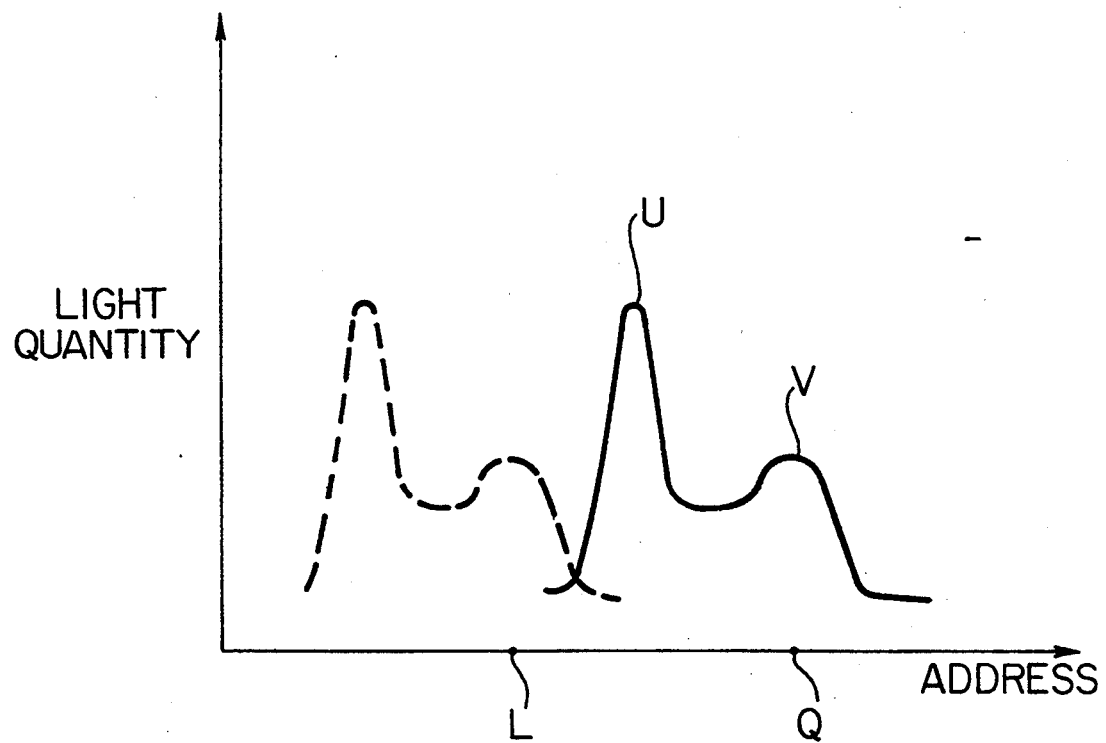
FIG. 9(a) is a view showing an intensity distribution of reflective light flux.
Figure 9B:
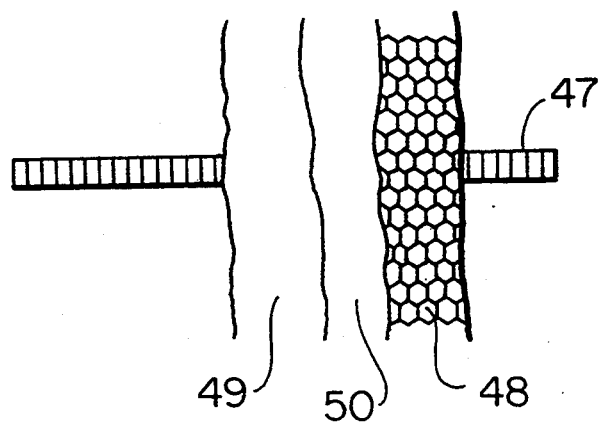
FIG. 9(b) is a view showing a sectional view of the cornea in a correspondence to the light flux distribution of FIG. 9(a)

The light flux reflected by the half mirror 41 is guided to a line sensor 47 acting as a sensor for detecting a focusing condition. The line sensor 47 is disposed as shown in FIG. 9(b) relative to the sectional direction of the cornea C. The intensity distribution of the reflection light flux corresponding to FIG. 9(b) is shown in FIG. 9(a). In FIG. 9(a), reference character U denotes a peak portion formed by the light flux reflected on the surface T of the cornea C. Reference character V denotes a peak portion formed by the light flux reflected on the endothelium portion of the cornea C. The peak portion U corresponds to the luminous image 49. The peak portion V corresponds to the luminous image 48. For peak detection, a suitable known means is used.

A video signal outputted from the line sensor 47 is inputted into a focus judgment circuit 47' shown in FIG. 1. The focus judgment circuit 47' is adapted to store the signals representative of the peaks U and V shown in FIG. 9(a). By means of operation processing, the focus judgment circuit 47' judges an address L of the peak portion V of the reflection light from the corneal endothelium and further judges whether or not this address L is coincident with a predetermined address Q of the line sensor 47. The apparatus optical system is set such that the corneal endothelium is focused when the address V of the peak portion V is coincident with the predetermined address Q.

Next, the photographing procedure will be described.

In order to observe the corneal endothelium, the apparatus optical system is aligned with the eye E. Then, a rough determination is made as to which part of the corneal endothelium is to be observed or photographed while observing the anterior portion, and that part of the corneal endothelium is actually observed or photographed.

Specifically, the apparatus optical system is moved in the X- and Y-directions by a drive means, not shown, in accordance with the information of the alignment detection sensor 4'. By doing this, the optical axis 01 of the apparatus optical system is aligned with the optical axis 02 of the eye E. Also, the apparatus optical system is driven such that the address L of the peak portion V detected by the one-dimensional line sensor 47 is coincident with a central address Q.

More specifically, the apparatus optical system is moved in a Z-direction by the drive means in accordance with the information of the focus judgment circuit 47', in order to effect the Z-direction alignment such that the optical system will focus on the corneal endothelium.

At this time, the optical path switch mirror 5 is in a position retracted from the optical path. Accordingly, the image of the anterior portion shown in FIG. 6 is displayed on the screen of the monitor unit. When the X- and Y-directions alignment has been completed, the luminous spot image R' (FIG. 6) is situated at the center of the annular pattern image 27. The alignment can also be made manually while determining the positional relation between the luminous spot image R' and the annular pattern image 27.

In the condition after tile completion of the alignment, the slit plate 34 and the cornea C are in generally conjugate relation relative to the projection lens 35, while the mask 42 and the cornea C are in generally conjugate relation relative to the objective lens 40.

Then, a desired light emitting diode 18 of the light source plate 17 of the optical system 14 is emitted. By doing this, the visual axis of the patient is directed in a desired direction. Since the image of the anterior portion is displayed on tile screen 25, there can be roughly determined as to which part of the corneal endothelium is to be observed or photographed.

When, for example, the light emitting diode 18a is to be emitted, the visual axis of the eye E is directed generally in the direction of the optical axis 01 of the optical system 1 as shown in FIG. 6 and therefore the endothelium at the central portion of the cornea C can be observed.

Figure 10:
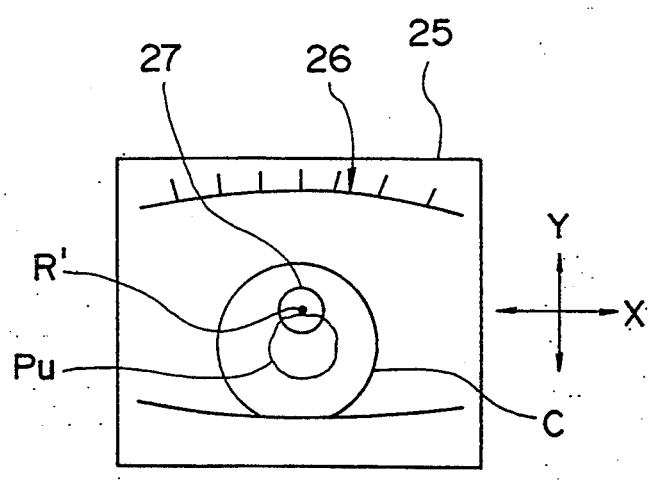
FIG. 10 is a schematic view showing an image of the anterior portion at the time the visual axis of the eye to be tested is directed downwardly.

Likewise, when, for example, a light emitting diode 18c positioned under the light emitting diode 18a is to be emitted (see FIG. 4), the visual axis of the eye E is directed downward as shown in FIG. 10 and therefore the endothelium at the upper part of the cornea C can be observed.

A number (or address) is attached to each light emitting diode 18. By recording this number (or address), the same photographing portion can easily be identified when that portion is to be measured again.

If an arrangement is made such that the dimension of the annular pattern image 27 is in generally coincident with that of the area within which the observing or photographing optical system 29 is capable of observing or photographing, the photographing portion can be correctly recognized even when the anterior portion is being observed.

The optical path switch mirror 5 is inserted into the optical path as shown by the solid line of FIG. 1, the light source 30 for the use of observation is emitted to split-illuminate the eye E with the infrared light, and the image of the corneal endothelium is observed under the reflected light. Then, visible light is emitted from the photographing light source 32 in order to photograph the endothelium.

What is claimed is:

1. An apparatus for photographing an endothelium of a cornea of an eye to be tested having an apparatus optical system comprising:
    an anterior portion observing optical system for observing an anterior portion of the eye to be tested;
    said anterior portion observing system having an optical axis normal to a reference plane tangent to an apex of the cornea of the eye;
    an illumination optical system for illuminating the cornea of the eye obliquely with respect to the optical axis of said anterior portion observing optical system;
    an observing or photographic optical system for observing or photographing the endothelium of the cornea by receiving the light reflected on the endothelium of the cornea obliquely with respect to the optical axis of said anterior portion observing optical system, said observing or photographing optical system being disposed at a position opposite to said illumination optical system with respect to the optical axis of said anterior portion observing optical system placed therebetween; and
    a fixation mark light projecting optical system capable of changing a position where a fixation mark is presented, in order to change a direction in which the eye is fixedly gazed.

2. An apparatus for photographing an endothelium of a cornea according to claim 1, wherein an angle formed between the optical axis of said anterior portion observing optical system and an optical axis of said illumination optical system is substantially equal to an angle formed between the optical axis of said anterior portion observing optical system and an optical axis of said observing or photographing optical system.

3. An apparatus for photographing an endothelium of a cornea according to claim 1, wherein said apparatus optical system comprises an alignment target light projection means for projecting alignment target light for aligning a vertical direction and a horizontal direction of said apparatus optical system relative to the cornea, and light receiving means for receiving the alignment target light reflected by the cornea.

4. An apparatus for photographing an endothelium of a cornea according to claim 3, wherein said anterior portion observing optical system has an image receiving element for receiving an image of the anterior portion and said apparatus optical system further comprises a pattern projecting system for projecting a ring-like pattern for alignment, said ring-like pattern being received in superimposed relation with the image of the anterior portion on the image receiving element.

5. An apparatus for photographing an endothelium of a cornea according to any one of claims 1 to 4, wherein said fixation mark light projecting system has a plurality of light sources, and one of the plurality of light sources can be selected to present the fixation mark.

6. An apparatus for photographing an endothelium of a cornea according to any one of claims 1 to 4, wherein said fixation mark light projecting system has at least one light source, and said one light source is movable so that a sight direction of the eye may be directed in other directions than that of an optical axis of said anterior portion observing optical system.

7. An apparatus for photographing an endothelium of a cornea according to claim 4, wherein the size of said ring-like pattern is generally equal to that of an observing or photographing part of the cornea.

8. An apparatus for photographing an endothelium of a cornea of an eye to be tested having an apparatus optical system comprising:
    an anterior portion observing optical system with a low magnification, for observing an anterior portion of the eye to be tested;
    an illumination optical system for illuminating the cornea of the eye; and
    a photographing optical system for photographing an endothelium of the cornea by receiving the light reflected on the endothelium of the cornea illuminated by said illumination optical system at a greater magnification than that of said anterior portion observing optical system;
    said apparatus optical system being provided with a fixation mark light projecting system capable of changing a position where a fixation mark is presented, in order to change a direction in which the eye is fixedly gazed.

9. An apparatus for photographing an endothelium of a cornea according to claim 8, wherein said apparatus optical system comprises an alignment target light projection means for projecting alignment target light for aligning a vertical direction and a horizontal direction of said apparatus optical system relative to the cornea, and light receiving means for receiving the alignment target light reflected by the cornea.

10. An apparatus for photographing an endothelium of a cornea according to claim 9, wherein said anterior portion observing optical system has an image receiving element for receiving an image of the anterior portion and said apparatus optical system comprises a pattern projecting system for projecting a ring-like pattern for alignment, said ring-like pattern being received in superimposed relation with the image of the anterior portion on the image receiving element.

11. An apparatus for photographing an endothelium of a cornea according to claim 9 or 10, wherein said fixation mark light projecting system has a plurality of light sources, and one of the plurality of light sources can be selected to present the fixation mark.

12. An apparatus for photographing an endothelium of a cornea according to claim 9 or 10, wherein said fixation mark light projecting system has at least one light source, and said one light source is movable so that a sight direction of the eye may be directed in other directions than that of the optical axis of said anterior portion observing optical system.

13. An apparatus for photographing an endothelium of a cornea according to claim 10, wherein the size of said ring-like pattern is generally equal to that of an observing or photographing part of the cornea.

* * * * *